United States Patent
Hasler et al.

(10) Patent No.: US 6,891,037 B1
(45) Date of Patent: May 10, 2005

(54) METHOD FOR THE ISOLATION OF POLYSACCHARIDES

(75) Inventors: Thomas Hasler, Bern (CH); Emil Fürer, Muri (CH)

(73) Assignee: Schweiz. Serum- & Impfinstitut Bern, Bern (CH)

(*) Notice: Subject to any disclaimer, the term of this patent is extended or adjusted under 35 U.S.C. 154(b) by 0 days.

(21) Appl. No.: 09/355,220

(22) PCT Filed: Jan. 20, 1998

(86) PCT No.: PCT/EP98/00268

§ 371 (c)(1),
(2), (4) Date: Oct. 6, 1999

(87) PCT Pub. No.: WO98/32873

PCT Pub. Date: Jul. 30, 1998

(30) Foreign Application Priority Data

Jan. 24, 1997 (EP) .............................. 97101143

(51) Int. Cl.$^7$ ................................. C07H 1/06
(52) U.S. Cl. .................... 536/127; 536/123.1; 536/124; 424/484
(58) Field of Search .............................. 536/123.1, 128, 536/127, 124; 424/484, 256.1, 249.1, 257.1

(56) References Cited

U.S. PATENT DOCUMENTS 5,589,591 A * 12/1996 Lewis

FOREIGN PATENT DOCUMENTS

EP 0 407 037 A1 1/1991

OTHER PUBLICATIONS

Hou et al. J. Parenteral Science & Technology, 1990. 44(4): 204–209.*
Schneerson et al. J. Exp. Med. 1980. 152: 361–376. (copy not provided since it was cited in the specification).*
Dubos, Rene, et al., "Human Immunity to the Meningococcus", Apr. 1, 1969, *Jln. Experimental Medicine* 129(4):1349–1365.

* cited by examiner

*Primary Examiner*—Jennifer E. Graser
(74) *Attorney, Agent, or Firm*—Pillsbury Winthrop LLP

(57) ABSTRACT

The invention relates to a method for the isolation of polysaccharides, in particular for the separation of endotoxins from capsule polysaccharides of gram-negative bacteria. The polysaccharides isolated by this method are preferably used for the production of polysaccharide vaccines. The invention furthermore relates to vaccines containing polysaccharides isolated by the method described in this invention.

14 Claims, No Drawings

METHOD FOR THE ISOLATION OF POLYSACCHARIDES

The invention relates to a method for the isolation of polysaccharides, in particular for the separation of endotoxins from capsule polysaccharides of gram-negative bacteria. The polysaccharides isolated by this method are preferably used for the production of polysaccharide based vaccines. The invention furthermore relates to vaccines containing polysaccharides isolated by the method described in this invention.

In producing vaccines, in particular polysaccharide vaccines from bacterial polysaccharides, the removal of endotoxins is a critical and decisive step during the purification of polysaccharides. The method for the separation of endotoxins from bacterial polysaccharides which is used most often according to the state of the art is based on the extraction with phenol, which, if necessary, has to be repeated several times until the endotoxin content is as required by health authorities. This method is complicated and time-consuming. In addition, working with phenol is troublesome and causes undesirable toxic waste. Moreover, the yields of polysaccharides obtainable by said methods known from the state of the art are often unsatisfactory. Other methods for the isolation of bacterial polysaccharides known from the state of the art are based on the use of affinity columns. These are often injurious to health (e.g. the use of column material containing polymyxin B). Furthermore, many column materials have only a limited capacity, which, for obtaining technically usable yields of polysaccharides, necessitates large and thus expensive columns (cf. e.g. U.S. Pat. No. 5,045,456; U.S. Pat. No. 5,039,610; and U.S. Pat. No. 5,034,519).

Therefore, the problem to be solved by the invention was to provide a method for the Isolation of polysaccharides which is simple, economically useful and less injurious to health. The solution to said problem is achieved by the embodiments characterized in the claims.

Thus, the invention relates to a method for the isolation of polysaccharides, wherein the following steps are carried out (a) mixing of a bacterial polysaccharide fraction with a detergent solution;

(b) addition of alcohol to a final concentration which is below the concentration at which the polysaccharide precipitates;

(c) mixing the solution;

(d) filtering the solution;

(e) separation of the polysaccharide from detergent and alcohol.

Bacterial polysaccharide fractions which can be used in the method of the invention can be produced by the methods known from the state of the art; cf. e.g. Gotschlich et al., J. Exp. Med. 129 (1969), 1349–1365 as well as Schneerson et al., J. Exp. Med. 152 (1980), 361–376. The concentration of alcohol at which the polysaccharide precipitates in the presence of a detergent solution can be determined by the person skilled in the art according to conventional methods. For example, this concentration can be determined by way of simple series of tests.

The reaction, i.e. the precipitation of the endotoxin from the polysaccharide solution, is conventionally carried out from 1 minute up to 1 hour; it can, however, be carried out for several hours. In contrast to the methods known from the state of the art, the method of the invention is simple, fast, inexpensive and causes less toxic waste. In addition, the yields of polysaccharide are considerably higher. The method of the invention is based on a selective precipitation of alcohol in the presence of at least one detergent which abolishes non-covalent interactions between polysaccharides, lipopolysaccharides and proteins.

In a preferred embodiment of the method of the invention the alcohol to be added is ethanol.

In a further preferred embodiment of the method of the invention the separation of the polysaccharide from detergent and alcohol is carried out by the precipitation of the polysaccharide by adding more alcohol.

This embodiment of the method is particularly preferred as the precipitation of the polysaccharide and thus the separation of detergents and alcohol can be achieved by simply adding more alcohol. In another embodiment, precipitation of the polysaccharide can be achieved by adding alcohol different from the one used in step (b).

A further preferred embodiment of the invention relates to a method, wherein the polysaccharides stem from gram-negative bacteria. In a particularly preferred embodiment the gram-negative bacteria are bacteria of the genus *Haemophilus, Neisseria, Klebsiella* or *Escherichia* and in particular of the species *Haemophilus influenzae* (type b), *Neisseria meningitidis, Klebsiella pneumoniae* or *Escherichia coli*. The polysaccharides here concerned are capsule polysaccharides.

The isolation of polysaccharides from bacteria of these genera and/or species is particularly preferred as these polysaccharides are suitable for use in the vaccination against the following diseases: meningitis, epiglottitis, otitis media, pneumonia, arthritis, sepsis, nosocomial infections, urinary tract infections and gastroenteritis.

In a further preferred embodiment of the method of the invention the detergent is an anionic surfactant. Particularly preferred is a method wherein the anionic surfactant is an alkyl sulfate, for example sodium dodecyl sulfate (SDS).

The advantage of the use of SDS in the method of the invention is i.a. that SDS is obtainable from a plurality of manufacturers at a favorable price.

In a further particularly preferred embodiment of the method of the invention the surfactant concentration in the solution added to the polysaccharide fraction in step (a) above is at the most 20% (w/w). As mentioned above, the surfactant is preferably an alkyl sulfate and for example SDS.

Particularly preferred as the method of the invention is a method wherein the surfactant concentration in the polysaccharide solution, for example the SDS concentration, is 0.1% to 4% (final concentration, w/w).

In an additional preferred embodiment of the method of the invention the alcohol is added in step (b) to the solution to a final concentration which is approximately 10% below the concentration at which the polysaccharide precipitates.

It has been found by way of empirical series of tests that the addition of alcohol in step (b) to this final concentration is particularly advantageous as the loss of polysaccharide in the presence of this concentration is small, and endotoxin nonetheless is efficiently precipitated.

In another preferred embodiment of the method of the invention the initial concentration of polysaccharides in the polysaccharide fraction is greater than 10 mg/ml.

While the method of the invention can as well be carried out at smaller concentrations of polysaccharides in the polysaccharide fraction, the above-mentioned concentration should be used as minimum concentration in the method of the invention, in particular for economic reasons.

In a further preferred embodiment, the method of the invention relates to a method wherein the filtration is carried out by means of a polymer filter.

In another preferred embodiment of the method of the invention, filtration is carried out by means of a deep bed filter.

In the context of the present invention, the term "deep bed filter" means a filter which in contrast to a membrane filter (2-dimensional) possesses a 3-dimensional structure (depth). This structure has the advantage that the deep bed filter has a high capacity of retaining particles and correspondingly does not become obstructed so fast.

In the present invention, the use of polymer or deep bed filters has proved is worth. In this context, it has to be noted that a polymer filter can as well be a deep bed filter, and vice-versa, a deep bed filter can be a polymer filter; this condition, however, is not obligatory.

The isolation of the polysaccharides according to the method of the present invention is particularly efficient when deep bed filters are used for filtration.

In a particularly preferred embodiment of the method of the invention the polymer filter and/or the deep bed filter is a polypropylene filter.

The invention further relates to a polysaccharide vaccine which comprises a polysaccharide isolated according to the method of the invention. Optionally, said polysaccharide vaccine also includes a pharmaceutically acceptable carrier. Examples of such carriers are tetanus toxoid, diphteria toxoid, Pseudomonas Exotoxin A and cholera toxin.

The polysaccharide vaccine of the invention, as can be taken from the above explanations, can be produced in a particular simple and inexpensive manner. In addition, its production is particularly unharmful for the laboratory staff's health. An example of the vaccine of the present invention is a vaccine based on meningococci polysaccharide. These as well as the below-mentioned embodiments of the vaccine of the invention are administered parenterally, the administration being effected one or several times and preferably (where not indicated differently) several times. Usually, the administration is effected intramuscularly or subcutaneously, wherein per dosis 1–50 µg polysaccharide are used.

The polysaccharide vaccine of the invention is particularly suitable for the vaccination against meningitis, epiglottitis, otitis media, pneumonia, arthritis, sepsis, nosocomial infections, urinary tract infections or gastroenteritis. Moreover, the vaccine of the invention can also be used for the vaccination against other diseases caused by gram-negative bacteria carrying capsule polysaccharides.

Furthermore, the invention relates to a conjugate consisting of a polysaccharide isolated according to the method of the invention and a pharmaceutically acceptable protein chemically connected therewith. Examples of such proteins are tetanus toxoid, diphteria toxoid, Pseudomonas Exotoxin A and cholera toxin. Preferred dosages comprise 1–20 µg of the conjugate.

Additionally, the invention relates to a conjugate vaccine comprising a polysaccharide isolated according to the method of the invention and a pharmaceutically acceptable protein chemically connected therewith.

The conjugate vaccine of the invention is preferably used for the immunization against or prophylaxis of the diseases mentioned above.

In this context, it is particularly preferred that the immunization is carried out with small children.

The invention further relates to a combination vaccine comprising a polysaccharide isolated according to the method of the invention or a conjugate of the invention as well as an additional immunogenic component, wherein the additional immunogenic component preferably induces an immune response against a pathogen different from the pathogen from which the polysaccharide stems. An example of a combination vaccine is a *Haemophilus influenzae* vaccine in which the corresponding polysaccharide is conjugated with tetanus toxoid. E.g. pertussis, diphteria, tetanus and hepatitis B components may additionally be formulated in said vaccine. Preferred dosages comprise 1–20 µg of polysaccharide in the combination vaccine, particularly preferred are 1–10 µg, for example in the case of the *Haemophilus influenzae* combination vaccine described above, of Haemophilis influenzae polysaccharide. Preferred dosages for diphteria components in said vaccine are 15–25 Lf (Limit of flocculation), for tetanus components 5–10 Lf and for pertussis components more than 4 IU (International Units). The person skilled in the art can determine the dosages/concentrations of additional components in the combination vaccine of the invention according to standard procedures/standard provisions. The combination vaccine of the invention is preferably administered only once.

The additional immunogenic component is preferably a diphteria, tetanus, pertussis, hepatitis B or poliomyelitis antigen.

Finally, the invention relates to the use of a polysaccharide isolated according to the method of the invention as intermediate product for the production of a conjugate or combination vaccine. Here, the intermediate product is chemically connected with a pharmaceutically acceptable protein so as to form a conjugate. Correspondingly, the invention preferably relates to a use, wherein the conjugate or combination vaccine comprises as an active component a conjugate comprising a polysaccharide isolated according to the method of the present invention and a pharmaceutically acceptable protein chemically connected therewith.

The examples illustrate the invention.

EXAMPLE 1

Isolation of a *Haemophilus influenzae* Type b Capsule Polysaccharide

A capsule polysaccharide fraction (PRP, polyribosylribitolphosphate) from *Haemophilus influenzae* type b processed according to conventional methods is mixed in a concentration of >10 mg/ml with a 4% SDS solution. Ethanol is then added to a final concentration which is about 10% below the concentration at which the polysaccharide begins to precipitate. The solution is mixed for about 20 minutes, time periods of from 1 minute to several hours also appearing suitable, followed by a slight turbidity.

Thereupon, filtration is effected by way of a polypropylene deep bed filter. By this filtration step, the endotoxins are separated and remain in the filter. It is to be expected that filtration as well as adsorption effects are responsible for the separation of the endotoxins. The filtered polysaccharide then precipitates by further adding ethanol, the SDS remaining in the solution. The precipitated polysaccharide can be separated from remaining SDS impurities by further ethanol precipitations. An additional processing of the polysaccharide as well as the fabrication as a vaccine, wherein the polysaccharide is preferably chemically connected with a suitable carrier protein, is carried out according to conventional methods known from the state of the art. In the preferred embodiment mentioned, the polysaccharide is also an intermediate product for a conjugate vaccine.

EXAMPLE 2

Isolation of *Neisseria meningitidis* Type (A) and (C) Capsule Polysaccharides

*Neisseria meningitidis* type (A) and (C) capsule polysaccharides were subjected to the same method steps as described in Example 1.

The yields of polysaccharides obtained by the methods described in Examples 1 and 2 are depicted in Tables I and II. It can be observed that the yield of *Haemophilus influenzae* type (b) capsule polysaccharides obtainable by the method of the invention is considerably higher than polysaccharide obtainable by methods known from the state of the art (phenol extraction).

TABLE I

Isolation of *H. influenzae* type b capsule polysaccharide (PRP)

| PRP Lot number[1] | Method | Amount of PRP (g) | Endotoxin before (EU/μg/PRP) | Endotoxin after (EU/μg/PRP) | Yield of PRP (%) |
|---|---|---|---|---|---|
| 27 | 5 × phenol | 8.3 | 475 | 26 | 67 |
| 627095 | EtOH/SDS | 1.9 | 72.5 | 0.11 | >95 |
| 611496 | EtOH/SDS | 75 | 55 | <0.05 | >95 |

[1]The lot numbers are numbers used internally by the applicant, CH-Serum. The lots were prepared according to conventional methods.

TABLE II

Isolation of *N. meningitidis* group C capsule polysaccharide (GCMP)

| GCMP Lot number[1] | Method | Amount of GCMP (g) | Endotoxin before (EU/μg/GCMP) | Endotoxin after (EU/μg/GCMP) | Yield of GCMP (%) |
|---|---|---|---|---|---|
| 150396 | EtOH/SDS | 7.3 | 46.8 | 7.7 | 92 |
| 905096 | EtOH/SDS | 7.5 | 258 | 1.1 | 77 |
| 906096 | EtOH/SDS | 7.8 | 85 | 0.1 | 67 |

What is claimed is:

1. A method for the isolation of polysaccharides, wherein the following steps are carried out:
    (a) mixing of a bacterial polysaccharide fraction with a detergent solution;
    (b) addition of alcohol to a final concentration at which endotoxins are precipitated and which is below the concentration at which the polysaccharide precipitates;
    (c) mixing the solution;
    (d) filtering the solution by way of a deep bed filter, wherein the endotoxins are separated and remain in the filter;
    (e) separation of the polysaccharide from detergent and alcohol.

2. The method of claim 1, wherein the alcohol is ethanol.

3. The method of claim 1, further wherein the separation of the polysaccharide from detergent and alcohol is carried out by the precipitation of the polysaccharide by adding more alcohol.

4. The method of claim 1, wherein the polysaccharides are capsule polysaccharides from gram-negative bacteria.

5. The method of claim 4, wherein the gram-negative bacteria are selected from the genera consisting of *Haemophilus, Neisseria, Klebsiella* and *Escherichia*.

6. The method of claim 1, wherein the detergent is an anionic surfactant.

7. The method of claim 6, wherein the anionic surfactant is an alkyl sulfate.

8. The method of claim 6, wherein the surfactant concentration in the solution added to the polysaccharide fraction in step (a) is at the most 20% (w/w).

9. The method of claim 8, wherein the surfactant concentration in the polysaccharide solution is 0.1% to 4% (final concentration, w/w).

10. The method of claim 1, wherein in step (b) the alcohol is added to the solution to a final concentration which is approximately. 10% below the concentration at which the polysaccharide precipitates.

11. The method of claim 1, wherein the initial concentration of polysaccharides in the polysaccharide fraction is greater than 10 mg/ml.

12. The method of claim 1, wherein the filtration is carried out by means of a polymer filter.

13. The method of claim 12, wherein the polymer filter is a polypropylene filter.

14. The method of claim 4, wherein the gram-negative bacteria is selected from the group consisting of *Haemophilus influenzae* (type b), *Klebsiella pneumoniae, Neisseria meningitidis* and *Escherichia coli*.

* * * * *